United States Patent [19]

Green

[11] Patent Number: 4,539,427

[45] Date of Patent: Sep. 3, 1985

[54] PROCESS FOR THE PREPARATION OF FORMAMIDES

[75] Inventor: Michael J. Green, Hedon, England

[73] Assignee: BP Chemicals Limited, London, England

[21] Appl. No.: 543,092

[22] Filed: Oct. 18, 1983

[30] Foreign Application Priority Data

Oct. 20, 1982 [GB] United Kingdom ............... 8229989
Dec. 16, 1982 [GB] United Kingdom ............... 8235844

[51] Int. Cl.³ .................... C07C 102/00; C07C 102/06
[52] U.S. Cl. ................................. 564/132; 564/135; 564/137
[58] Field of Search ...................... 564/132, 135, 137

[56] References Cited

U.S. PATENT DOCUMENTS 3,763,234 10/1973 Brill .............................. 564/137 X

FOREIGN PATENT DOCUMENTS 0080349 5/1982 Japan ................................ 564/137

OTHER PUBLICATIONS

Smathers, CA 89: 196987g, (1978).

Primary Examiner—Thomas A. Waltz
Attorney, Agent, or Firm—Brooks, Haidt, Haffner & Delahunty

[57] ABSTRACT

Formamides e.g. diethylformamide are prepared by reacting a primary or secondary amine e.g. diethylamine or ammonia with (a) an alkyl formate or (b) carbon monoxide and an alkanol in the presence, as catalyst, of (i) a compound containing an amidine group or (ii) a Group V element-containing Lewis base and an epoxide. The Lewis base can be a trivalent nitrogen or phosphorus-containing compound. The amidine group which can be cyclic or acyclic can form part of a guanidine group.

8 Claims, No Drawings

PROCESS FOR THE PREPARATION OF FORMAMIDES

This invention relates to a process for the production of formamides, more particularly to N-substituted formamides such as N,N-dimethylformamide.

Formamides, for example N,N-dimethyl formamide and N,N-diethylformamide are useful chemicals in industry and have wide application as industrial solvents.

At the present time dimethylformamide is prepared from dimethylamine, carbon monoxide and methanol. In one process the carbon monoxide and methanol are first reacted to form methyl formate which is then reacted with the dimethylamine to form the dimethylformamide. In another process the carbon monoxide is reacted with the dimethylamine in the process of sodium methoxide and methanol to form the dimethylformamide.

It has now been found that a catalyst system comprising a compound containing an amidine group or a Lewis base and an epoxide is effective for the above mentioned reactions to form formamides.

According to the present invention a process for the preparation of formamides comprises reacting a primary or secondary amine or ammonia with
(a) an alkyl formate or
(b) carbon monoxide and an alkanol in the presence, as catalyst, of (i) a compound containing an amidine group or (ii) a Group V element-containing Lewis base and an epoxide promoter.

The primary or secondary amine can be of the formula $R^1R^2NH$ where $R^1$ and $R^2$, which can be the same or different are hydrogen atoms or hydrocarbyl groups e.g. $C_1$ to $C_{10}$ alkyl groups.

Conveniently the formate is a $C_1$ to $C_{12}$ alkyl formate, or is an aralkyl formate, for example benzyl, and the $R^1$ and $R^2$ groups are conveniently $C_1$ to $C_{12}$ hydrocarbyl groups. Conveniently the alkanol is a $C_1$ to $C_{12}$ alkanol, preferably a primary or secondary alcohol.

Conveniently the alkanol is present in an amount from 5 to 95% by weight of the reaction mixture.

By Group V is meant the group of elements comprising nitrogen, phosphorus, arsenic, antimony and bismuth.

Conveniently the Lewis base is an organic compound containing trivalent phosphorus or trivalent nitrogen, for example of formula $R_3X$ where X is nitrogen or phosphorus and R is hydrogen or a monovalent organic group containing up to 12 carbon atoms. The R groups can be the same or different.

In the case of nitrogen the Lewis base can be an amine for example a primary, secondary or tertiary amine and can be the primary or secondary amine used as one of the reactants.

The Lewis base can be an amidine. When this is the case it is not essential to employ an epoxide, although the epoxide will promote the action of the amidine.

By the term amidine is meant the grouping:

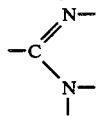

Conveniently the free valencies on the nitrogen atoms are attached to carbon atoms or hydrogen and the free valency on the carbon atom to another carbon atom or nitrogen atom. In the last mentioned case the structure will comprise a guanidine grouping.

The amidine group-containing compound can be cyclic or acyclic. The amidine group can be directly attached to a ring or form part of a heterocyclic ring in particular a fused ring system. For example the amidine can be 1,5-diazabicyclo[4.3.0] non-5-ene or 1,8diazabicyclo[5.4.0] undec-7-ene, or 1,5,7-triazabicyclo[4.4.0] dec-5-ene.

Suitable trivalent phosphorus-containing compounds are trialkyl and triaryl phosphines which can optionally contain more than one phosphorus atom.

The epoxide can be a 1:2 alkylene oxide such as ethylene oxide, 1:2 propylene oxide, 1:2 butylene oxide and the like.

Conveniently the molar proportions of Lewis base to epoxide are from 1:10 to 20:1, preferably 1:1 to 10:1.

Since the epoxide can react with the ammonia or amine reactant it is preferred that the catalyst has substantially no free epoxide present when contacted with the ammonia or amine reactant. This can be achieved by contacting the epoxide with the Lewis base and allowing to substantially completely react, and/or removing unreacted epoxide prior to contacting the ammonia or amine reactant. The reaction between epoxide and Lewis base can be effected in the presence of an alkanol (which can be the alkanol reactant) and be assisted by heating e.g. up to about 100° C. optionally under superatmospheric pressure.

The process is conveniently effected at a temperature in the range 20° to 150° C. and for example from 1 bar to 150 bar.

Convenient molar proportions of carbon monoxide to alkanol and carbon monoxide to amine are such that excess carbon monoxide is present over that required for complete conversion of the amine to the formamide.

It is possible, by adjustment of the reaction conditions, to produce not only the formamide but also varying amounts of an alkyl formate of formula $HCOOR^3$ where $R^3$ is a $C_1$ to $C_{12}$ alkyl (which $C_1$ to $C_{12}$ alkyl is the alkyl of the $C_1$ to $C_{12}$ alcohol).

The process of the present invention can employ ammonia or primary or secondary amines and is particularly suitable for preparing, formamide itself where $R^1R^2NH$ is ammonia, n-propylformamide where $R^1R^2NH$ is n-propylamine, dimethylformamide where $R^1R^2NH$ is dimethylamine and diethylformamide where $R^1R^2NH$ is diethylamine respectively.

The invention is illustrated by the following Examples.

In all the Examples, the reactants and products were maintained in the liquid phase and the catalyst were employed in solution.

Examples 1 to 20 illustrate the use, as catalyst, of a Lewis base and an epoxide promoter.

EXAMPLE 1

Preparation of diethyl formamide and methyl formate

A solution containing 26 g of methanol, 1.3 g of 1:2 butene oxide, and 1 g of 1,5-diazabicyclo[4.3.0]non-5-ene (DBN) was allowed to stand at room temperature for 1 hour to allow the DBN and epoxide to react, after which time 7.5 g of diethylamine was added and the resulting solution was transferred to a 100 ml high pressure stirred autoclave. The autoclave was sealed, pressurized to 49 bar with carbon monoxide, and finally heated to 90° C. with stirring (1200 rpm). Rapid gas absorption occurred and the pressure was maintained between 49 and 60 bar by replenishment from a cylinder. After 30 min, the autoclave was cooled to 0° C. Analysis of the liquid product by gas chromatography showed a quantitative diethylamine conversion with a selectivity to diethyl formamide of 90% (and a 35% conversion of methanol to methyl formate).

EXAMPLE 2

Preparation of di-n propyl formamide and methyl formate

Example 1 was repeated except that 1.4 g of 1:2 propene oxide was used in place of butene oxide and 7.5 gm of di-n-propylamine was used in place of diethylamine. Analysis of the liquid product showed a quantitative conversion of dipropylamine with a selectivity to di-n-propyl formamide of 99% (and a 39% conversion of methanol to methyl formate).

EXAMPLE 3

Preparation of n-butyl formamide

Example 2 was repeated except that 5 g of n-butylamine was used in place of di-n-propylamine. Analysis of the liquid product showed a quantitative conversion of n-butylamine with a selectivity to n-butyl formamide of 97%.

EXAMPLE 4

Preparation of diethyl formamide and methyl formate

Example 1 was repeated except that 1.4 g of 1:2 propene oxide was used in place of butene oxide and the premixed catalyst solution was allowed to stand for 20 h at room temperature to allow substantially complete reaction between the epoxide and DBN prior to the addition of diethylamine. Analysis of the liquid product showed a quantitative conversion of diethylamine with a selectivity to diethyl formamide of 94% (and a 60% conversion of methanol to methyl formate).

EXAMPLE 5

Preparation of diethyl formamide and methyl formate

Example 4 was repeated except that the reaction was carried out at 60° C. for 3 hours. Analysis of the liquid product showed a quantitative conversion of diethylamie with a selectivity to diethyl formamide of 92% (and a 24% conversion of methanol to methyl formate).

EXAMPLE 6

Preparation of diethyl formamide and methyl formate.

Example 4 was repeated except that the excess 1:2 propene oxide (which had not reacted with DBN) was removed by purging with nitrogen immediately before the addition of diethylamine to improve selectivity. Analysis of the liquid product showed a quantitative conversion of diethylamine, with a selectivity to diethyl formamide of 99% (and a 57% conversion of methanol to methyl formate).

EXAMPLE 7

Preparation of diethyl formamide

Example 4 was repeated except that 2.8 g of 1:2 propene oxide was used and 1.1 g of 1,5,7-triazabicyclo[4.4.0]dec-5-ene was employed as the catalyst in place of DBN. Analysis of the liquid product showed a quantitative conversion of diethylamine with a selectivity to diethyl formamide of 98%.

EXAMPLE 8

Preparation of diethyl formamide and methyl formate

Example 4 was repeated except that 1.2 g of 1,8-diazabicyclo[5.4.0]undec-7-ene was used as a catalyst in place of DBN. Analysis of the liquid product showed a quantitative conversion of diethylamine with a selectivity to diethyl formamide of 90% (and a 12% conversion of methanol to methyl formate).

EXAMPLE 9

Preparation of n-propyl formamide and methyl formate

Example 4 was repeated except that 7.5 g of n-propylamine was used in place of diethylamine. Analysis of the liquid product showed a total conversion of n-propylamine to n-propyl formamide (and a 54% conversion of methanol to methyl formate).

EXAMPLE 10

Preparation of diethyl formamide and methyl formate

Example 4 was repeated except that 2 g of N,N'-dicyclohexyl-N''[2,2,6,6-tetramethylpiperidinyl] guanidine was used as a catalyst in place of DBN and the reaction time was increased to 3 h. Analysis of the liquid product showed a total conversion of diethylamine with a selectivity of diethyl formamide of 93% (and a 4% conversion of methanol to methyl formate).

EXAMPLE 11

Preparation of diethyl formamide

Example 4 was repeated except that 2.1 g of triphenylphosphine was used as a catalyst in place of DBN. Analysis of the liquid product showed a diethylamine conversion of 39% with a selectivity to diethyl formamide of 93%.

EXAMPLE 12

Preparation of dimethyl formamide

A solution containing 26 g of methanol, 1.4 g of 1:2 propene oxide and 2.1 g of triphenylphosphine was heated to 100° C. in a sealed Fischer-Porter tube under an initial nitrogen pressure of 50 psi. The tube was cooled to 5° C., and the liquid contents were transferred to the autoclave described in Example 1 together with 7.5 g of dimethylamine. The autoclave was sealed, pressurized to 50 bar with carbon monoxide, and finally heated to 90° C. Rapid gas absorption occurred and the pressure was maintained between 50 and 66 bar by replenishment from a cylinder. After 1 hour, the autoclave was cooled to 0° C. Analysis of the liquid product showed a quantitative dimethylamine conversion with a selectivity to dimethyl formamide of 97%.

EXAMPLE 13

Preparation of dimethyl formamide.

Example 12 was repeated except that 1.6 g of bis(diphenylphosphine) ethane was used as a catalyst in place of triphenylphosphine. Analysis of the liquid product showed a total conversion of dimethylamine to dimethyl formamide.

EXAMPLE 14

Preparation of dimethyl formamide.

Example 12 was repeated except that 1.6 g of tributylphosphine was used as a catalyst in place of triphenylphosphine. Analysis of the liquid product showed a total conversion of dimethylamine to dimethyl formamide.

EXAMPLE 15

Preparation of dimethyl formamide and methyl formate

Example 12 was repeated except that 1 g of triethylamine was used as a catalyst in place of triphenylphosphine. Analysis of the liquid product showed a total conversion of dimethylamine to dimethyl formamide (and a 39% conversion of methanol to methyl formate).

EXAMPLE 16

Preparation of dimethyl formamide

Example 12 was repeated except that 1.15 g of tri-n-propylamine was used as a catalyst in place of triphenylphosphine. Analysis of the liquid product showed a total conversion of dimethylamine to dimethyl formamide.

EXAMPLE 17

Preparation of dimethyl formamide and methyl formate

Example 12 was repeated except that 0.66 g of 1-methylimidazole was used as a catalyst in place of triphenylphosphine. Analysis of the liquid product showed a quantitative conversion of dimethylamine with a selectivity to dimethyl formamide of 92% (and a 15% conversion of methanol to methyl formate).

EXAMPLE 18

Preparation of dimethyl formamide

Example 12 was repeated except that 0.64 g of pyridine was used as a catalyst in place of triphenylphosphine. Analysis of the liquid product showed a quantitative conversion of dimethylamine with a selectivity to dimethyl formamide of 89%.

EXAMPLE 19

Preparation of dimethyl formamide and methyl formate

Example 12 was repeated except that 0.59 g of diethylamine was used as a catalyst in place of triphenylphosphine. Analysis of the liquid product showed a quantitative conversion of dimethylamine with a selectivity to dimethyl formamide of 79% (and a 20% conversion of methanol to methyl formate).

COMPARATIVE EXPERIMENT A

Example 5 was repeated in the absence of 1:2 propene oxide. Analysis of the liquid product showed a diethylamine conversion of only 10% and a methanol conversion of less than 1%

COMPARATIVE EXPERIMENT B

Example 12 was repeated in the absence of 1:2 propene oxide. Analysis of the liquid product showed a dimethylamine conversion of only 1.5%.

These two experiments when compared with Examples 5 and 12 illustrate the promotional effect of an epoxide.

EXAMPLE 20

Preparation of diethyl formamide

A solution containing 13 g of methanol, 0.7 g of 1:2 propene oxide, and 0.5 g of triethylamie was heated to 100° C. in a sealed Fischer-Porter tube under an initial nitrogen pressure of 50 psi. The tube was cooled to 5° C., and the liquid contents were transferred to a 100 ml conical flask. 15 g of methyl formate was added, followed by 5 g of diethylamine. Analysis of the liquid product after 15 min showed a quantitative conversion of diethylamine to diethyl formamide.

COMPARATIVE EXPERIMENT C

Example 20 was repeated in the absence of propene oxide. Analysis of the liquid product showed a diethylamine conversion of 31% to diethyl formamide.

The advantage of employing the above described catalysts systems comprising a Group V element-containing Lewis base and an epoxide is that they are highly soluble in both the reactants and products, and as a consequence will reduce or avoid deposition of solids in, for example, heat exchange equipment as compared with conventional catalysts such as sodium methoxide where there can be a major operational problem.

Examples 21 to 33 illustrate the use, as catalyst, of an amidine in the absence of an epoxide promoter.

EXAMPLE 21

A 100 ml high pressure stirred autoclave was charged with 20.7 g of methanol, 5.8 g of diethylamine, and 3.5 g of 1,5,7-triazabicyclo[4.4.0]dec-5-ene (TBD) as catalyst. The autoclave was sealed and flushed twice with carbon monoxide, following which it was pressurized to 50 bar with carbon monoxide and finally heated to 110° C. with stirring (1200 rpm). Rapid gas absorption occurred. The pressure was maintained between 46 and 56 bar by replenishment from a cylinder. After 15 min gas absorption had ceased and the autoclave was cooled to 0° C. Analysis of the liquid product showed that all the diethylamine had been converted to diethyl formamide, and that 30% of the methanol had been converted to methyl formate.

EXAMPLE 22

Example 21 was repeated except that the temperature was maintained at 80° C. for 3 hours. Analysis of the liquid product showed a quantitative conversion of diethylamine to diethylformamide (and a 55% conversion of methanol to methyl formate).

EXAMPLE 23

Example 21 was repeated with a reactor charge consisting of 10 g of methanol, 20 g of diethylamine and 4 g of TBD. After 1 hour gas absorption had ceased and the autoclave was cooled to 0° C. Analysis of the liquid product showed a quantitative conversion of diethylamine to diethylformamide (and a 25% conversion of methanol to methyl formate.

EXAMPLE 24

Example 21 was repeated except that 3.7 gm of 1,8-diazabicyclo[5.4.0]undec-7-ene (DBU) was used as a catalyst in place of TBD. After 3½ hours gas absorption had ceased and the autoclave was cooled to 0° C. Analysis of the liquid product showed a total conversion of diethylamine to diethylformamide (and 16% conversion of methanol to methyl formate).

EXAMPLE 25

Example 24 was repeated except that 3.0 g of 1,5-diazabicyclo[4.3.0]non-5-ene was used in place of DBU and the reaction was carried out at 130° C. Analysis of the liquid product showed a total conversion of diethylamine to diethylformamide (and a 12% conversion of methanol to methyl formate).

EXAMPLE 26

The autoclave described in Example 21 was charged with 25 g of methanol, 10 gm of dimethylamine, and 4.4 g of DBU. It was pressurized to 86 bar with carbon monoxide and heated to 130° C. with stirring (1200 rpm). Rapid gas absorption occurred. The pressure was maintained between 86 and 96 bar by replenishment from a cylinder. After 2 hours gas absorption had ceased and the autoclave was cooled to 0° C. Analysis of the liquid product showed a total conversion of dimethylamine to dimethylformamide (and a 21% conversion of methanol to methyl formate).

EXAMPLE 27

Example 26 was repeated except that 2 gm of TBD was used as a catalyst in place of DBU and the reaction was carried out at 120° C. for 10 min. Analysis of the liquid product showed a total conversion of dimethylamine to dimethylformamide (and a 39% methanol conversion to methyl formate).

EXAMPLE 28

The autoclave described in Example 21 was charged with 25 g of methanol, 15 g of di-n-butylamine, and 4.4 g of DBU. The autoclave was sealed and pressurised to 50 bar with carbon monoxide, following which it was heated to 130° C. with stirring (1200 rpm). The pressure in the autoclave was maintained between 48 and 58 bar by replenishment from a cylinder. After 3 hours gas absorption had ceased and the autoclave was cooled to 0° C. Analysis of the liquid product showed that all the di-n-butylamine had been converted to di-n-butylformamide (and that 12% of the methanol had been converted to methyl formate).

EXAMPLE 29

Example 28 was repeated except that 15 g of n-butylamine was used in place of di-n-butylamine. Analysis of the product mixture showed that all the n-butylamine had been converted to n-butylformamide (and that 5% of the methanol had been converted to methyl formate).

EXAMPLE 30

Example 28 was repeated except that 15 g of n-propylamine was used in place of di-n-butylamine. Analysis of the product mixture showed a total conversion of n-propylamine to n-propylformamide (and a 16% methanol conversion to methyl formate).

COMPARATIVE EXPERIMENT D

The autoclave described in Example 21 was charged with 15 g of methanol and 15 g of diethylamine. The autoclave was sealed and flushed twice with carbon monoxide, following which it was pressurised to 50 bar with carbon monoxide and heated to 120° C. for 3 hours with stirring (1200 rpm). Analysis of the liquid product showed a diethylamine conversion to diethylformamide of less than 1%.

This example shows that in the absence of the amidine catalyst the conversion of diethylamie is very low—less than 1% compared with 100% in Example 21.

COMPARATIVE EXPERIMENT E

Example 4 was repeated in the absence of methanol. Analysis of the liquid product showed a diethylamine conversion of less than 1%.

This example shows that the presence of an alcohol is essential.

EXAMPLE 31

The autoclave described in Example 21 was charged with 26 g of methanol, 7.5 g of diethylamine, and 5 g of N,N'-dicyclohexyl-N"[2,2,6,6-tetramethyl-piperidinyl] guanidine. It was sealed and pressurised to 50 bar with carbon monoxide, following which it was heated to 120° C. with stirring (1200 rmp). The pressure in the autoclave was maintained between 53 and 65 bar by replenishment from a cylinder. After 3 hours, gas absorption had virtually ceased and the autoclave was cooled to 0° C. Analysis of the liquid product showed that all the diethyl amine had been converted to diethyl formamide (and that 20% of the methanol had been coverted to methyl fomrate).

EXAMPLE 32

7.5 g of diethylamine, 26 g of methyl formate, and 1 g of TBD were mixed together in a 100 ml conical flask at room temperature and atmospheric pressure for 1 hour. Subsequent analysis of the liquid product showed that all the diethylamine had been converted to diethyl formamide.

COMPARATIVE EXPERIMENT F

Example 32 was repeated in the absence of TBD. Analysis of the product mixture showed a diethylamine conversion of only 29%.

This example shows that the amidine has a catalytic effect on the reaction between an alkyl formate and an amine.

EXAMPLE 33

Example 21 was repeated except that 20.7 g of n-propanol was used in place of methanol and the reaction time was increased to 30 min. Analysis of the liquid product showed a total conversion of diethylamine to diethyl formamide (and a 13% conversion of n-propanol to n-propyl formate).

The advantage of employing the above described amidine catalysts is that the catalysts themselves, their formate and carbonate salts are highly soluble in both reactants and products, and reduce the problem of solids deposition referred to above.

I claim:

1. A process for the preparation of formamides which process comprises reacting a primary amine or a secondary amine or ammonia with
    (a) an alkyl formate or an aralkyl formate or
    (b) carbon monoxide and an alkanol in the presence, as catalyst, of (i) a compound containing an amidine group or (ii) a Group V element-containing Lewis base and an epoxide promoter.

2. A process as claimed in claim 1 wherein the epoxide is contacted with the Lewis base before contacting the amine or ammonia.

3. A process as claimed in claim 1 wherein the Lewis base is an organic compound containing trivalent nitrogen or trivalent phosphorus.

4. A process as claimed in claim 1 wherein the catalyst comprises a compound containing an amidine group and an epoxide promoter.

5. A process as claimed in claim 1 wherein the amidine group forms part of a ring system.

6. A process as claimed in claim 5 wherein the ring system is a fused ring system containing six and five membered rings, or six and seven membered rings, or two six membered rings.

7. A process as claimed in claim 1 wherein the amidine group forms part of a guanidine group.

8. A process as claimed in claim 1 wherein the temperature is from 20° to 150° C. and the pressure from 10 to 150 bar.

* * * * *

UNITED STATES PATENT AND TRADEMARK OFFICE
CERTIFICATE OF CORRECTION

PATENT NO. : 4,539,427

DATED : September 3, 1985

INVENTOR(S) : MICHAEL JAMES GREEN

It is certified that error appears in the above-identified patent and that said Letters Patent is hereby corrected as shown below:

Col. 2, line 54, "catalyst" should read --catalysts--

Col. 3, lines 47-48, "diethylamie" should read --diethylamine--

Col. 6, line 5, "triethylamie" should read --triethylamine--

Col. 8, line 22, "(1200 rmp)" should read --(1200 rpm)--

Col. 8, line 29, "methyl fomrate" should read --methyl formate--

Signed and Sealed this

Tenth Day of December 1985

[SEAL]

*Attest:*

DONALD J. QUIGG

*Attesting Officer*  *Commissioner of Patents and Trademarks*